United States Patent
Tanaka et al.

[11] Patent Number: 5,637,105
[45] Date of Patent: Jun. 10, 1997

[54] ABSORBENT ARTICLE

[75] Inventors: Masahito Tanaka; Yayoi Fukuhara; Minoru Nakanishi, all of Tochigi-ken, Japan

[73] Assignee: Kao Corporation, Tokyo, Japan

[21] Appl. No.: 261,950

[22] Filed: Jun. 20, 1994

[30] Foreign Application Priority Data

Jun. 21, 1993 [JP] Japan ................. 5-149521

[51] Int. Cl.$^6$ ............... A61F 13/15; A61F 13/20
[52] U.S. Cl. ............... 604/368; 604/367; 604/372
[58] Field of Search ............... 604/358, 367–368, 604/372, 378, 385.1

[56] References Cited

U.S. PATENT DOCUMENTS

| | | | |
|---|---|---|---|
| 3,881,489 | 5/1975 | Hartwell | 604/382 |
| 5,387,208 | 2/1995 | Ashton | 604/372 |

FOREIGN PATENT DOCUMENTS

| | | |
|---|---|---|
| 0422504 | 4/1991 | European Pat. Off. . |
| 3525379 | 1/1987 | Germany . |
| 54-124398 | 8/1979 | Japan . |
| 57-1340 | 1/1982 | Japan . |
| 58-180602 | 10/1983 | Japan . |
| 61-45753 | 3/1986 | Japan . |
| 597914 | 4/1993 | Japan . |

OTHER PUBLICATIONS

English Language Abstract of Japanese Patent 4279160, dated Oct. 5, 1992.

English Language Abstract of German Patent DE 3525379A1 dated Jan. 22, 1987.

*Primary Examiner*—John G. Weiss
*Assistant Examiner*—P. Zuttarelli
*Attorney, Agent, or Firm*—Birch, Stewart, Kolasch & Birch, LLP

[57] ABSTRACT

An absorbent article having a liquid permeable topsheet, a liquid impermeable backsheet, an absorbent member interposed between the topsheet and backsheet, and a moisture absorbent material, wherein the amount of moisture absorption per unit area of the absorbent article is not less than $7.2 \times 10^{-4}$ g/hr.cm$^2$, and a total amount of moisture absorption of the absorbent article is not less than 0.10 g/hr in an environment of 35° C./75% RH.

7 Claims, 1 Drawing Sheet

ABSORBENT ARTICLE

BACKGROUND OF THE INVENTION

1. Field of the Invention

This invention relates to an absorbent article, such as a disposable diaper, an incontinence pad or a sanitary napkin, which is excellent in hygroscopicity (moisture absorbent property) and free from an uncomfortable feeling during use, such as stuffiness or stickiness, and to a method for controlling the humidity and the rise of the humidity in the area of the absorbent article during wear.

2. Description of the Prior Art

In a well-known manner, an absorbent article comprises a liquid permeable surface material, a liquid impermeable antileakage material and an absorbent member interposed therebetween for absorbing and retaining the liquid. The functions required of the absorbent article are to absorb excreted body fluid quickly and to prevent the return of the absorbed body fluid. Up to now, a variety of proposals, centered about these functions, has been made.

Recently, there has also been a demand for various functions concerning the feeling of the absorbent article during use. For example, it is strongly desired that the color of the body fluid diffused into the absorbent member be concealed and that the surface of the absorbent article in direct contact with the user's skin be similar to a cloth in both appearance and touch, and soft in feeling. As for feeling, inter alia, it has become a crucial task to reduce the stuffiness and stickiness of the absorbent article worn by the user.

The absorbent article is used in such a manner that it is in contact with a particular portion of the user's body for a prolonged period of time. In accordance with the improved absorbent performance of the absorbent article in recent years, the article tends to be used for prolonged period of time, so that the need to reduce stuffiness and stickiness is more strongly felt, than the need for improved feeling. That is, if the article is not improved with respect to stuffiness and stickiness, the skin in contact with the absorbent article is subjected to thermal stress for a prolonged period of time, and undergoes bloating under high humidity, such that, in the worst case, skin troubles, such as itching or a rash are produced to the extent that the user cannot continue to wear the absorbent article.

There has also been proposed a variety of techniques of improving a topsheet as a method for combatting the stuffy or sticky feel. For example, there has been proposed a technique of employing a non-woven fabric of an agglomerated mass of hydrophobic fine fibers, as a surface material for the topsheet, for creating a hydrophobic space between the body surface and the absorbent article, thereby improving the fluid retention property without impairing liquid permeability (Japanese Patent Laid-open Publication No. 58-180602). There has also been proposed a technique of improving the fluid retention property of the absorbent article by using a hydrophobic sheet, more specifically a film, having apertures, as a surface material for the topsheet (Japanese Utility Model Laid-open Publications Nos. 54-124398, 57-1340 and 61-45753). In sum, these prior-art techniques combat the stuffiness and stickiness by improving the fluid retention property, by preventing the body fluid absorbed into the absorbent article from seeping into the space between the topsheet and the skin in order to diminish the opportunity for body fluid to come into direct contact with the skin.

However, it is only possible with the above-described prior-art techniques to reduce the opportunity for body fluid to come into direct contact with the skin. That is, the prior-art techniques do not prevent the moisture taken up by the absorbent article from being vaporized under body temperature and dissipated towards the skin or do not remove the moisture transpired from the skin as vapor. Even granting that the liquid retention properties of the above-described prior-art techniques could be raised to the maximum so that the liquid return could be reduced substantially to zero, it is essentially impossible to eliminate the stuffiness or stickiness inherent in the absorbent article.

SUMMARY OF THE INVENTION

It is therefore a principal object of the present invention to provide an absorbent article, such as a disposable diaper, an incontinence pad or a sanitary napkin which, by effectively diminishing the humidity in the area of the absorbent article during wear, has a comfortable feeling, is free from stuffiness or stickiness and does not cause skin irritation, such as itching or a rash.

As a result of research, the present inventors have found that the above object can be achieved by providing the absorbent article with a moisture absorbent material (hygroscopic material) so that the amount of moisture absorption of the absorbent article can be maintained in more than a preset amount.

The present invention has been obtained on the basis of the above finding, and provides an absorbent article having a liquid permeable topsheet, a liquid impermeable backsheet and an absorbent member interposed between the topsheet and backsheet, wherein the improvement comprises that the absorbent article has a moisture absorbent material, such that the amount of moisture absorption per unit area of the absorbent article is not less than $7.2 \times 10^{-4}$ g/hr cm$^2$, and the total amount of moisture absorbed by the absorbent article is not less than 0.10 g/hr in an environment of 35° C./75% RH (relative humidity).

Further, according to the present invention, the above-mentioned object can be achieved by providing an absorbent article comprising a moisture absorbent material and a moisture permeable sheet having a specified moisture permeability, wherein the amount of moisture absorption of the absorbent article is maintained at more than a preset amount and the moisture is allowed to be discharged gradually.

That is, the present invention provides for an absorbent article having a moisture absorbent material, and a liquid impermeable backsheet comprising a moisture permeable sheet exhibiting a moisture permeability of not less than 0.7 g/100 cm$^2$.hr, wherein the amount of moisture absorption per unit area of the absorbent article is not less than $7.2 \times 10^{-4}$ g/hr.cm$^2$, and a total amount of moisture absorption of the absorbent article is not less than 0.10 g/hr in an environment of 35° C./75% RH.

The present invention also provides a method for controlling the humidity in the area of the absorbent article during wear, comprising controlling the rise in humidity in the environment between the absorbent article and the skin to not higher than 70% RH by absorbing the moisture transpired from the user with a moisture absorbent material of the absorbent article and by discharging the absorbed moisture outwardly away from the skin of a user via a liquid impermeable backsheet, during the time the user wears the absorbent article.

The absorbent article of the present invention, such as a disposable diaper, an incontinence pad or a sanitary napkin, has a fine wearing feel, and is free from an uncomfortable feeling, such as stickiness or stuffiness, and does not cause skin troubles, such as itching or a rash, by effectively diminishing the humidity in the vicinity of the absorbent article during wear.

DETAILED DESCRIPTION OF THE DRAWINGS

Figure 1:
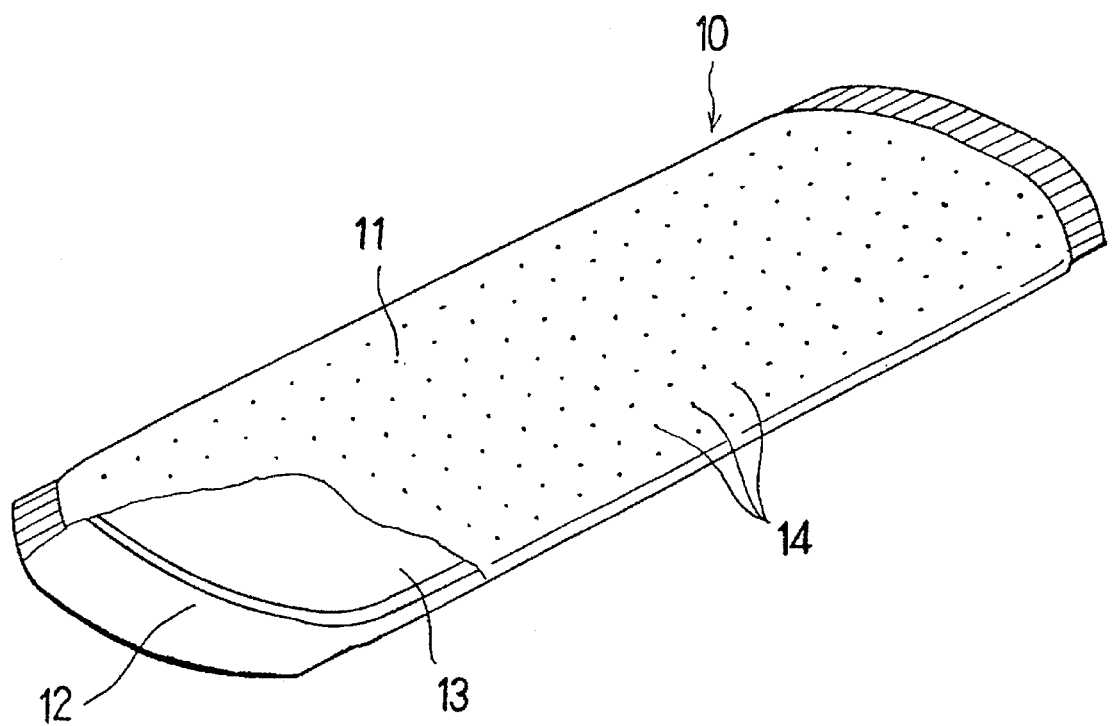
FIG. 1 is a perspective view showing an absorbent article embodying the present invention, with a portion thereof being broken away.

An absorbent article according to the present invention will be explained in detail hereinbelow.

The liquid permeable topsheet and the absorbent member, as components of the absorbent article of the present invention, may be any of those commonly employed in absorbent articles. Examples of the absorbent article of the present invention includes a disposable diaper, an incontinence pad and a sanitary napkin with or without flaps.

The absorbent article of the present invention has a moisture absorbent material, and a liquid impermeable backsheet comprising a moisture permeable sheet having a particular moisture permeability. The absorbent article of the present invention has a preset amount of moisture absorption whereby the skin surface of the user is perpetually maintained in a dry state.

The specific preset amount of the moisture absorption of the absorbent article of the present invention depends on the size of the absorbent article, that is on the area of the body surface actually covered by the absorbent article. However, for unity of expression, it is most desirably expressed in terms of the amount of moisture absorption per unit area. According to the present invention, the amount of moisture absorbed per unit area of the absorbent article is not less than $7.2 \times 10^{-4}$ g/hr.cm$^2$, preferably in a range of from $3.0 \times 10^{-3}$ g/hr.cm$^2$ to $7.0 \times 10^{-3}$ g/hr.cm$^2$, under an environment of 35° C./75% relative humidity (RH).

The amount of moisture absorbed by the absorbent article in its entirety depends on its size, as mentioned hereinabove. In the case of the regular type sanitary napkin, for example, it is not less than 0.10 g/hr and is preferably in a range of from 0.35 to 1.00 g/hr, under an environment of 35° C./75% relative humidity (RH). If the amount of moisture absorption is less than 0.10 g/hr, the humidity of the body surface in contact with the absorbent article is undesirably raised with the lapse of wearing time even in the absence of excretion of body fluid.

There is no particular limitation as to the moisture absorbent material employed in the present invention. It is however desirable for the moisture absorbent material to be free of components that are harmful or irritating to the skin or the human body. If the moisture absorbent material contains water-soluble components, there is a risk that these components will dissolve in the body fluid that is brought into contact with the user's skin. It is therefore desirable that water-insoluble material or insolubilized water-soluble material be used as the moisture absorbent material.

The amount of moisture absorption per hour of the moisture absorbent material is not less than 0.08 g/g*hr, preferably not less than 0.10 g/g*hr, more preferably in a range of from 0.20 to 1.20 g/g*hr and most preferably in a range of from 0.35 to 1.20 g/g*hr. If the amount of moisture absorption is less than 0.08 g/g*hr, it becomes necessary to use as much as several grams of the moisture absorbent material in order to obtain a sufficient moisture absorption capability, which is impractical with respect to both the cost and the weight of the resultant absorbent article.

Among the water-insoluble materials, as the above-mentioned moisture absorbent materials, there are the following three types of materials (1) to (3):

(1) inorganic/organic porous materials capable of adsorbing moisture on its surface, such as activated charcoal, natural or artificial silica or synthetic zeolite;

(2) hydrophilic polymers, namely (i) well-known highly absorbent polymers, such as cross-linked sodium polyacrylate, starch-polyacrylic acid graft polymer, or a copolymer of a monomer having carboxylate, sulfonate or sulfate groups and a monomer having phosphate or phosphonate groups, and (ii) hydrophilic polymers other than the above-mentioned highly absorbent polymers, such as non-cross-linked sodium polyacrylate, carboxyl methyl cellulose (CMC), polyvinyl pyrrolidone or polyvinylsulfone; and (3) non-water-soluble organic/inorganic hydrophilic gel, such as silica gel, which becomes swollen by absorbing the moisture as a vapor and also as a liquid.

The above-mentioned highly absorbent polymers exhibit moisture absorbing and discharging properties, that is, the polymers absorb and discharge moisture repeatedly. Therefore, if the highly absorbent polymers are used as the moisture absorbent materials and the moisture permeable sheet, which will be described later, is used as the liquid impermeable backsheet, the moisture once absorbed and retained may be discharged away from the user's skin through the moisture permeable sheet to keep the user's skin in a desirably dry state at all times. The moisture absorbing and discharging material, as disclosed for example in Japanese Patent Laid-open Publication No. 5-97914, may be employed simultaneously as the moisture permeable sheet and the liquid impermeable backsheet.

Among the water-soluble materials, as the above-mentioned moisture absorbent materials, there are, for example, deliquescent salts, such as lithium chloride or sodium hydroxide, substances that chemically take up moisture, such as diphosphorus pentaoxide, metal sodium, calcium oxide or iron powders, and substances that take up moisture as crystal water, such as copper chloride or anhydrous copper sulfate. Although the substances that chemically take up moisture include substances generally accepted as being water insoluble, such as calcium hydroxide, iron oxide or iron hydroxide, the substances that chemically take up moisture need to be insolubilized because the smallest amount of ions resulting from solution thereof in water affects the human body in some form or other.

For insolubilizing the above-mentioned water-soluble materials, these materials may be coated either alone or as a composite or mixture with a polymer having high vapor permeability, such as non-crystalline polyethylene, polystyrene or polypropylene. Alternatively, the materials are wrapped in a thin film formed from the above-mentioned polymer. The polymer may be of a unitary structure, a block polymer of plural polymers or a copolymer of plural monomers.

As the thin film employed for the above objective, a so-called moisture permeable sheet, having numerous fine apertures and exhibiting high vapor permeability, may be advantageously employed.

It suffices to use the moisture absorbent material in such an amount that the amount of moisture absorbed by the absorbent article in its entirety is within the range as mentioned before. If, for example, the highly absorbent polymer is employed as the moisture absorbent material for the sanitary napkin, the moisture absorbent material is employed, in an amount of not less than 0.7 g, preferably in an amount not less than 1.0 g, more preferably in an amount of 1.5 to 10 g, and most preferably in an amount of 2 to 10 g. If the moisture absorbent material is used in an amount less than 0.7 g, the moisture absorbent properties are undesirably lowered when the material absorbs the body fluid such as meno-blood. If it is used in an amount exceeding 10 g, the absorbent article is undesirably lowered in pliability.

The amount of the highly absorbent polymer as required per unit area of the absorbent article is preferably not less than $5.0 \times 10^{-3}$ g/cm$^2$ and more preferably $1.5 \times 10^{-2}$ g/cm$^2$ to $7.6 \times 10^{-2}$ g/cm$^2$.

The absorbent article has the moisture absorbent material in any of the following four forms;

(1) The liquid permeable topsheet or the absorbent member is produced from the moisture absorbent material;

(2) The moisture absorbent material is mixed or dispersed in the material of the absorbent member;

(3) A moisture absorbent member is produced from the moisture absorbent material and the moisture absorbent member is unified with the absorbent member; and (4) A moisture absorbent member is interposed between the liquid permeable topsheet and the absorbent member or between the absorbent member and the liquid-impermeable backsheet.

Form (1) may be implemented by employing a hydrophilic film as a topsheet, or by employing hydrophilic polyurethane or a foamed copolymer of a monomer having carboxylate, sulfonate or sulfate groups and a monomer having phosphate or phosphonate groups as an absorbent member.

Form (2) may be implemented by employing a non-woven fabric having moisture absorbent hydrophilic fibers mixed therein, or by mixing or dispersing a well-known highly absorbent polymer, such as cross-linked sodium polyacrylate or a starch- polyacrylic acid graft copolymer, into the absorbent member.

Above all, mixing the highly absorbent polymer into the absorbent member is effective and desirable for obtaining good antileakage property, because the highly absorbent polymer is a moisture absorbent material and has superior properties as an absorbent material.

Form (3) may be implemented by mounting a moisture absorbent member comprising a piece of the moisture absorbent material wrapped in a vapor-permeable film on the lower part of the absorbent member and as one with the absorbent member, by mounting a porous piece of the moisture absorbent member as one with the absorbent member on the top or within the inside of the absorbent member, or by molding a moisture absorbent member having the moisture absorbent material encapsulated and dispersed within the moisture absorbent member.

Forms (2) and (3) may also be implemented by employing a vapor permeable film sandwiching the moisture absorbent material therebetween or a vapor-permeable film having the moisture absorbent material dispersed inside thereof as the backsheet of each of the above-mentioned absorbent members.

Form (4) may be implemented by mounting a moisture absorbent member as a separate member between the liquid permeable topsheet and the absorbent member.

Although hydrophilic fiber material used extensively as the absorbent member, such as pulp or rayon, exhibits moisture absorbent properties (hygroscopicity) in the broad sense of the term, it does not exhibit sufficient moisture absorbent properties to diminish the stuffy or sticky feeling. However, such material may be processed into a moisture absorbent material capable of satisfying the above-mentioned desirable amount of moisture absorption by drying to a critical point. The process of "drying to a critical point" means the process of compulsorily drying the fiber material to an extreme point or a critical point to forcibly raise its moisture absorbent capacity.

That is, if the conventional absorbent article is placed in an evacuated environment, that is, in a state of being dried to a critical point, and subsequently encapsulated in a wrapping material rich in gas barrier properties, such as a thick film of high crystalline polyethylene or a Saran resin film, the absorbent member formed of pulp or the like can be processed into a moisture absorbent member comprising a moisture absorbent material capable of satisfying the above-mentioned amount of moisture absorption.

As the liquid impermeable backsheet, as a component member of the absorbent article of the present invention, any of the sheets commonly employed as the backsheet of the absorbent article may be employed without limitation. However, a moisture permeable sheet is most preferably employed.

As examples of such moisture permeable sheets, sheets having numerous small-sized holes and exhibiting high vapor permeability are employed. Preferably used, for example, is a sheet having pores and exhibiting high vapor permeability produced by uni-axially or bi-axially stretching a polyethylene film having mixed and kneaded thereinto inorganic powders of calcium carbonate or barium sulfate and an incompatible organic high-molecular material, such as nylon or polystyrene.

An example of such a moisture permeable sheet is a moisture permeable film with a basis weight of 13 to 28 g/m$^2$, which is produced by stretching a polyethylene film, with a basis weight of 20 to 50 g/m$^2$, containing 30 to 60 wt % of calcium carbonate having a mean particle size of 0.5 to 1.0 µm, to a double length in a MD direction.

As the moisture permeable sheet, a water-repellent non-woven fabric or a composite sheet of the above polyethylene sheet and the water-repellent non-woven fabric may be employed.

The moisture permeability of the moisture permeable sheet is preferably not less than 0.7 g/100 cm$^2$.hr and more preferably 1.0 to 4.0 g/100 cm$^2$.hr. Such a value of moisture permeability is preferred because when the moisture permeability is less than 0.7 g/100 cm$^2$.hr, the sheet becomes a barrier and retards the gradual discharge of moisture to the outside.

An absorbent article having the moisture permeable sheet as the backsheet has the function of lowering the humidity during excretion, compared with an absorbent article having the moisture impermeable sheet as the backsheet. However, since there may be cases that it is not possible to suppress rapid rise in humidity in the area of the absorbent article during wear, i.e., caused by movements and/or perspiration of the user or when the function of lowering the humidity becomes substantially nil due to a large quantity of excretion, it is preferable to employ the moisture permeable sheet having the above-defined moisture permeability.

An absorbent article making use of only the moisture absorbent material displays the function of absorbing moisture during excretion to lower humidity quickly, and hence is superior in the amount of moisture decrease per unit time compared to an absorbent article making use of only the moisture permeable backsheet. However, it may occur with an absorbent article making use of only the moisture absorbent material that its function in lowering the moisture is gradually lost in case of a large amount of excretion.

On the other hand, with an absorbent article having both the moisture absorbent material and the moisture permeable sheet, the moisture absorbent material displays the effect of suppressing the moisture caused by perspiration and/or excretion in a shorter time at the initial period of use of the absorbent article. Besides, the moisture retained by the moisture absorbent material and any excess moisture are gradually discharged via the moisture permeable sheet out of the absorbent article. Therefore, sufficient effects may be sustained during prolonged use and upon the occasion of a large amount of excretion.

Further, with an absorbent article making use of both the moisture absorbent material and the moisture permeable sheet, desired effects can be obtained even if the amount of moisture absorption is set to a lower value than within the above range.

The method of the present invention for controlling the humidity in the area of the absorbent article is hereinafter explained.

The method resides in controlling the rise in humidity in the environment between the user and the absorbent article to not higher than 70% RH by absorbing the moisture transpired from the user with a moisture absorbent material of the absorbent article and by discharging the absorbed moisture away from the user via a liquid impermeable backsheet.

The term "moisture" as used herein means not only the moisture, that is water and vapor, transpired from the user, but also the moisture derived from the excretion absorbed by the absorbent article.

The expression "discharging away from the user" means that the moisture is expelled away from the user through the side of the absorbent article which does not contact the skin of the user via the liquid impermeable backsheet of the absorbent article.

The control method according to the present invention may preferably be carried out by utilizing the above-mentioned absorbent article of the present invention, above all, the absorbent article of the present invention in which the moisture permeable sheet having the above-defined moisture permeability is used as the liquid impermeable backsheet.

Since the absorbent article of the present invention has the above-mentioned moisture absorbent material, the moisture transpired by the user can be effectively absorbed in the above-defined amount of moisture absorption. In addition, if the liquid impermeable backsheet is the above-mentioned moisture permeable sheet having the above-defined moisture permeability, the moisture may be effectively discharged away from the user at the above-defined moisture permeability.

With the humidity controlling method of the present invention, the rise in humidity in the environment between the user and the absorbent article can be controlled to be not higher than 70% RH and preferably in a range of from 35 to 65% RH.

DESCRIPTION OF EXAMPLES

The present invention will now be explained with reference to Examples and Comparative Examples. However, the present invention is not limited to these Examples.

Example 1

25 μm of low-density polyethylene, manufactured by Mitsui Petorochemical Industries, Ltd. under the trade name of Ultzex 15101C, was laminated on a dry thermally bonded non-woven fabric, with the basis weight of 25 g/m$^2$, formed of polyethylene/polypropylene composite fibers, manufactured by CHISSO KK under the trade name of NBF, having deposited thereon a surfactant comprised of a mixture of alkyl phosphate and sorbitan-fatty acid ester in an amount of 0.34 wt %. The resultant laminated product was perforated under heating to produce a topsheet material having holes 0.1 to 2 mm$^2$ in size formed therein at a density of 52/cm$^2$.

Using the topsheet thus obtained, a sanitary napkin shown in FIG. 1 was produced. In FIG. 1, showing a sanitary napkin 10 as an embodiment of the absorbent article of the present invention by a partially severed perspective view, the sanitary napkin 10 is made up of a topsheet 11 having holes 14 formed by the above-mentioned topsheet material, a backsheet 12 formed by a liquid impermeable antileakage sheet, having polyethylene laminated thereon, an absorbent member 13 formed by a pulp sheet interposed between the topsheet 11 and the backsheet 12 and having the density of 0.06 g/cm$^2$, basis weight of 300 g/m$^2$ and a thickness of 5 mm and a hot-melt adhesive for preventing slip, not shown in the Figures.

The sanitary napkin was placed into a vacuum oven and was evacuated overnight. This process is termed the process of drying to a critical point. After the process of drying to a critical point was completed, the sanitary napkin was taken out of the oven and quickly put into a polyethylene pouch having a wall thickness of 40 μm. The opening of the pouch was heat-sealed to give an inventive article 1.

Example 2

A sanitary napkin was produced in the same way as in Example 1, except using an absorbent member, 175 mm long and 70 mm wide, produced by unitarily holding 2 g of a super absorbent polymer (moisture absorbent material comprising sodium polyacrylate), manufactured by Kao Corporation under the trade name of Wonder Gel, with an absorbent paper sheet with the basis weight of 33 g/m$^2$, to give an inventive article 2.

Example 3

A sanitary napkin was prepared which had a structure similar to that of Example 1, except using an absorbent member prepared by uniformly dispersing 3 g of silica gel (moisture absorbent material) previously processed by drying to a critical point into a pulp sheet having a density of 0.06 g/cm$^2$, a basis weight of 300 g/m$^2$ and a thickness of 5 mm, manufactured by WAKO JUN-YAKU KK. The resulting product was quickly put into a polyethylene pouch having a wall thickness of 40 μm and the opening of the pouch was heat-sealed to give an inventive article 3.

Example 4

A sanitary napkin was prepared which had a structure similar to that of Example 1, except using an absorbent member in which a moisture absorbent member, 175 mm long, 70 mm wide and 1.5 mm thick, prepared by sealing 1 g of lithium chloride (moisture absorbent material) with a moisture permeable film having a moisture permeability of 1.7 g/100 cm$^2$.hr, was mounted as one in the lower part of a pulp sheet having a density of 0.06 g/cm$^2$, basis weight of 300 g/m$^2$ and a thickness of 5 mm, to give an inventive article 4.

Example 5

In a sheet 175 mm long, 70 mm wide and 1.5 mm thick, prepared by sealing 1 g of lithium chloride (moisture absorbent material) with a moisture permeable film having a moisture permeability of 1.7 g/100 cm$^2$.hr, a number of holes 5 mm in diameter were formed in a random manner. A porous moisture absorbent member having holes at a density of 1.5/cm$^2$ on the whole and having the internal lithium chloride not exposed to outside was prepared by heat-sealing hole edge portions. The porous moisture absorbent member was sandwiched between two pulp sheets having a density of 0.06 g/cm$^2$, basis weight of 300 g/m$^2$ and a thickness of 2.5 mm, and these were bonded integrally to yield an absorbent member. A sanitary napkin was prepared in the same way as in Example 1, except using the absorbent member thus prepared, to give an inventive article 5.

Example 6

Using the topsheet produced in Example 1, a sanitary napkin shown in FIG. 1 was produced. In FIG. 1, showing a sanitary napkin 10 as an embodiment of the absorbent article of the present invention by a partially severed perspective view, the sanitary napkin 10 is made up of a topsheet 11 having holes 14 formed by the above-mentioned topsheet material, a backsheet 12 formed by a liquid impermeable moisture permeable sheet, an absorbent member 13, 175 mm long and 70 mm wide, formed by unitarily holding 1.3 g of a super absorbent polymer, manufactured by Kao Corporation under the trade name of Wonder Gel, interposed between the topsheet 11 and the backsheet 12, by an absorbent paper having the basis weight of 33 g/m$^2$, and a hot-melt adhesive to prevent slippage, not shown in Figures, to give an inventive article 6.

As the backsheet 12, formed by the moisture permeable sheet, a moisture permeable film, with a basis weight of 20 g/m$^2$, obtained by stretching a polyethylene film, with the basis weight of 40 g/m$^2$, containing 45 wt % of calcium carbonate having a mean particle size of 0.7 µm, to a double size in the MD directions, was employed.

Example 7

A sanitary napkin was prepared which had the structure similar to that of Example 6, except using an absorbent member prepared by uniformly dispersing 1.8 g of silica gel, manufactured by WAKO JUN-YAKU KK, previously processed by drying to a critical point into a pulp sheet having a density of 0.06 g/cm$^2$, a basis weight of 300 g/m$^2$ and a thickness of 5 mm. The resulting product was quickly put into a polyethylene pouch having a thickness of 40 µm and the opening of the pouch was heat-sealed to give an inventive article 7.

Example 8

A sanitary napkin was prepared in the same way as in Example 6, except using an absorbent member in which a moisture absorbent member, 175 mm long, 70 mm wide and 1.5 mm thick, prepared by sealing 0.5 g of lithium chloride (moisture absorbent material) with a moisture permeable film having a moisture permeability of 1.7 g/100 cm$^2$.hr, was mounted as one with a pulp sheet and in the lower part of the pulp sheet having a density of 0.06 g/cm$^2$, basis weight of 300 g/m$^2$ and a thickness of 5 mm, to give an inventive article 8.

Example 9

In a sheet 175 mm long, 70 mm wide and 1.5 mm thick, prepared by sealing 0.2 g of lithium chloride (moisture absorbent material) with a moisture permeable film having a moisture permeability of 1.7 g/100 cm$^2$.hr, a number of holes 5 mm in diameter were formed in a random manner. A porous moisture absorbent member having holes at a density of 1.5/cm$^2$ on the whole and having the internal lithium chloride not exposed to outside was prepared by heat-sealing hole edge portions. The porous moisture absorbent member was sandwiched between two pulp sheets having a density of 0.06 g/cm$^2$, basis weight of 300 g/m$^2$ and a thickness of 2.5 mm, and these were bonded integrally, to give an absorbent member. A sanitary napkin was prepared in the same way as in Example 6, except using the absorbent member thus prepared, to give an inventive article 9.

Comparative Example 1

The procedure of Example 1 was followed except the process of drying to the critical point and subsequent steps were not performed, to give a comparative article 1.

Comparative Example 2

A sanitary napkin was produced in the same way as in Example 1, except using an absorbent member, 175 mm long and 70 mm wide, comprising 0.2 g of a super absorbent polymer, manufactured by Kao Corporation under the trade name of Wonder Gel, sandwiched between absorbent paper sheets having a basis weight of 33 g/m$^2$, to give a comparative article 2.

Comparative Example 3

A sanitary napkin was produced in the same way as in Example 6, except using a pulp sheet having the density of 0.06 g/m$^2$, basis weight of 300 g/m$^2$ and a thickness of 5 mm as an absorbent member to give a comparative article 3.

Comparative Example 4

A sanitary napkin was produced in the same way as in Example 6 except using an absorbent member, 175 mm long and 70 mm wide, comprising 0.2 g of a super absorbent polymer, manufactured by Kao Corporation under the trade name of Wonder Gel, sandwiched between absorbent paper sheets having a basis weight of 33 g/m$^2$, to give a comparative article 4.

Of the inventive and comparative articles obtained as described above, the amounts of moisture absorption per hour, humidity control effects in the area of the absorbent article and the wearing feel were evaluated. The amount of moisture absorbed by the moisture absorbent material A, the amount of the moisture absorption of the sanitary napkin A', the humidity control effects in the area of the absorbent article, expressed as the mean value of the humidity h0 directly after wearing, in % RH, humidity h1 after lapse of two hours after wearing, in % RH, and changes in the humidity before and after the attachment δh, in % RH, results of evaluation of the wearing feel by (a) stickiness, (b) stuffiness and (c) feel on the whole, are shown in Table 1 for the inventive articles 1 to 5 and comparative articles 1 and 2, and in Table 2 for the inventive articles 6 to 9 and the comparative articles 3 to 5. The methods of the evaluation are also shown below.

1) Amount of Moisture Absorption per Hour

For measuring the amount of moisture absorbed by the moisture absorbent material, an electronic balance capable of weighing up to 0.01 g, manufactured by Mettler Instrumente AG under the trade name of PM 4000, was placed in a variable-environment chamber set to 35° C./75% RH.

After the balance was sufficiently accustomed to the environment, the moisture absorbent material, precisely weighed in advance, was set thereon and allowed to stand for two hours. If the gain in weight during the time period of two hours and the weight of the original moisture absorbent material are given as w1 and w0, respectively, the amount of the absorbed moisture A may be found by the equation:

$$A[g/g*hr] = w1[g]/w0[g]*2[hr]$$

Although the amount of the moisture absorbed by the sanitary napkin A' may be determined by the similar technique, such amount A' may be found by the following equation in this case:

$$A'[g/hr] = w1[g]/2[hr]$$

Further, the amount of the absorbed moisture per unit area A" may be found by the following equation, based on the area of the used absorbent member S:

$$A''[g/cm^2 \cdot hr] = w1[g]/S[cm^2].2[hr]$$

2) Humidity control Effects in the User's Wearing Portion

Samples of the sanitary napkins were attached at the monitors' crotches and temperature/humidity sensors, manufactured by DAIICH KAGAKU KK under the trade name of THP 13, were inserted between the skin contacting surfaces of the samples and the skin of the user. If the sanitary napkins were sealed in the polyethylene pouches, as in Example 1, the sanitary napkins were taken out of the pouches directly before measurement. The humidity in the environment of the monitors' skin was measured directly after the attachment by the monitors, after lapse of 2.0 hours from the time of attachment of the inventive articles 1 to 5 and the comparative articles 1 and 2, and after a lapse of 2.0 hours or 3.5 hours from the time of attachment. Similar measurements were made on 20 female monitors and mean values of the humidity directly after the attachment h0 [% RH], the humidity after a lapse of 3.5 hours after the attachment h1 [% RH] and changes in humidity before and after attachment δh [% RH] were found and used as the indices for the humidity control effects in the area of the absorbent article.

3) Evaluation of the Wearing Feel

The samples of the sanitary napkins were worn by the monitors under usual conditions for two hours or longer for the inventive articles 1 to 5 and the comparative articles 1 and 2, for three hours or longer for the inventive articles 6 to 9 and the comparative articles 3 to 5. Then, the wearing feel were evaluated using direct inquiry and answer method on the following items a) to c).

a) stickiness
1- sticky
2- slightly sticky
3- medium
4- slightly unsticky
5- not sticky b) stuffiness
1- stuffy
2- slightly stuffy
3- medium
4- slightly unstuffy
5- not stuffy c) overall wearing feeling
1- bad
2- slightly bad
3- medium
4- slightly good
5- good In the inquiry and answer method, the monitors were requested to select the numbers corresponding to the monitors' sense most appropriately. The inquiry and answer method was conducted for 20 monitors and the mean values of the selected numbers were found for the respective items. These mean values substantially have the following meanings for the respective items.

a) stickiness

The smaller the mean value, the more sticky the article is. The mean value of 3 is medium. If the mean value is larger than 3, the article is less sticky.

b) stuffiness

The smaller the mean value, the more stuffy the article is. The mean value of 3 is medium. If the mean value is larger than 3, the article is less stuffy.

c) overall wearing feeling

The smaller the mean value, the worse is the wearing feel. The mean value of 3 is medium. If the mean value is larger than 3, the better is the wearing feel.

TABLE 1

| | Moisture absorbent material | A [g/g*hr] | A' [g/hr] | A" [g/cm²hr] | h0 [% RH] | h1 [% RH] | δh [% RH] | Feeling evaluation a) | b) | c) |
|---|---|---|---|---|---|---|---|---|---|---|
| Inventive articles | | | | | | | | | | |
| 1 | pulp dried to a critical point | 0.20 | 0.30 | $2.3 \times 10^{-3}$ | 40 | 65 | +25 | 3.5 | 3.7 | 3.0 |
| 2 | super absorbent polymer | 0.30 | 0.60 | $4.6 \times 10^{-3}$ | 40 | 38 | −2 | 4.5 | 4.5 | 4.2 |
| 3 | silica gel | 0.20 | 0.55 | $4.2 \times 10^{-3}$ | 33 | 55 | +22 | 3.4 | 3.2 | 3.0 |
| 4 | lithium chloride | 0.60 | 0.60 | $4.6 \times 10^{-3}$ | 36 | 30 | −6 | 4.8 | 5.0 | 5.0 |
| 5 | lithium chloride | 0.60 | 0.44 | $3.4 \times 10^{-3}$ | 40 | 35 | −5 | 4.5 | 4.6 | 4.5 |
| Comp. | | | | | | | | | | |

TABLE 1-continued

|  | Moisture absorbent material | A [g/g*hr] | A' [g/hr] | A" [g/cm²hr] | h0 [% RH] | h1 [% RH] | δ h [% RH] | Feeling evaluation a) | b) | c) |
|---|---|---|---|---|---|---|---|---|---|---|
| articles | | | | | | | | | | |
| 1 | none | 0.05 | 0.07 | 5.3 × 10⁻⁴ | 60 | 90 | +20 | 1.2 | 1.2 | 1.0 |
| 2 | super absorbent polymer | 0.30 | 0.08 | 5.3 × 10⁻⁴ | 60 | 80 | +20 | 1.3 | 1.2 | 1.1 |

TABLE 2

|  | Moisture absorbent material | Moisture permeability 1) | A [g/g*hr] | A' [g/hr] | A" [g/cm²hr] | h0 [% RH] | h1 [% RH] | δ h [% RH] | Feeling evaluation a) | b) | c) |
|---|---|---|---|---|---|---|---|---|---|---|---|
| Inventive articles | | | | | | | | | | | |
| 6 | super absorbent polymer | 1.7 | 0.30 | 0.40 | 3.0 × 10⁻³ | 40 | 39 | −1 | 4.0 | 4.0 | 3.9 |
| 7 | silica gel | 1.7 | 0.20 | 0.35 | 2.7 × 10⁻³ | 33 | 62 | +29 | 3.0 | 3.0 | 3.0 |
| 8 | lithium chloride | 1.7 | 0.60 | 0.30 | 2.3 × 10⁻³ | 36 | 32 | −4 | 4.5 | 4.5 | 4.2 |
| 9 | lithium chloride | 1.7 | 0.60 | 0.13 | 9.9 × 10⁻⁴ | 40 | 60 | +20 | 3.2 | 3.4 | 3.0 |
| Comp. articles | | | | | | | | | | | |
| 3 | none | 1.7 | 0.05 | 0.05 | 3.8 × 10⁻⁴ | 55 | 82 | +27 | 1.2 | 1.2 | 1.0 |
| 4 | super absorbent polymer | 1.7 | 0.30 | 0.07 | 5.3 × 10⁻⁴ | 52 | 80 | +28 | 1.0 | 1.2 | 1.0 |

1) Unit of Moisture Permeability is g/100 cm² · hr.

It is seen from the results shown in Table 1 that, by using an absorbent member having an amount of moisture absorption per hour in excess of 0.2 g/g*hr, the sanitary napkin has an amount of moisture absorption of not less than 0.2 g/hr. Thus it is seen that a sanitary napkin having the moisture absorbing function suppresses the humidity in environment in the area of the absorbent article to a lower value for an extended time of two hours. Above all, with the napkins employing a larger amount of the moisture absorbent material having superior moisture absorbing properties, such as the highly absorbent polymers or lithium chloride, as the napkins of Examples 2, 4 and 5, the humidity environment in the area of the absorbent article remain substantially unchanged from the time of attachment until a lapse of two hours, thus indicating that the skin feel the user had when she wore the napkin is maintained as long as she is wearing the napkin. With the napkin not having special moisture absorbing functions, the humidity after lapse of two hours rises to a hardly bearable level of 80 to 90%. Correspondingly thereto, the skin feel of the sanitary napkin of Examples 2, 4 and 5 is very good, whereas it is extremely poor for the sanitary napkins of Comparative Examples not having special moisture absorbent functions. Thus it is seen that, in order to have the skin feel at least higher than the medium level, the amount of moisture absorption needs to be 0.2 g/hr or more, as with the sanitary napkins of Examples 1 and 3.

As seen from the results of Table 2, it is possible for the sanitary napkin having both the moisture absorbing function and the moisture permeable function to maintain the humidity within the area of the absorbent article for a longer time interval of 3.5 hours. It is also seen that, with the napkin employing a larger quantity of the moisture absorbent material having superior moisture absorbent properties, such as the highly absorbent polymer or lithium chloride, above all, the napkins of Examples 6 and 8, the humidity in environment in the area of the absorbent article remains substantially unchanged even after a lapse of 3.5 hours from the time of attachment, such that the skin feel the user had when she wore the napkin is maintained as long as she is wearing the napkin. If the napkin has no specified moisture absorbent function and only has the moisture permeability function, moisture displacement occurs due to the vapor pressure difference between the inside and the outside of the napkin, and a discharge of a sufficient quantity of moisture is not produced within a shorter time so that the humidity within the area of the absorbent article cannot be suppressed sufficiently.

Thus it is seen that the samples of the sanitary napkins of Examples 6 to 9 give extremely good skin touch and hence are capable of affording fine use feeling and maintaining a dried state perpetually in the private parts of the user, as compared with the sanitary napkins of the Comparative Examples in which one of the moisture absorbent function or the moisture permeability function is insufficient.

Although the foregoing description has been made with reference to the sanitary napkin, the present invention may also be applied to other types of the absorbent articles, such as disposable diapers or incontinence pad.

What is claimed is:

1. A sanitary napkin comprising a liquid permeable topsheet, a liquid impermeable backsheet, an absorbent member interposed between said topsheet and said backsheet, said absorbent member comprising a super absorbent polymer moisture absorbent material in an amount 0.7 g to 10 g, wherein the amount of said super absorbent polymer per unit area is not less than $5.0 \times 10^{-3}$ g/cm$^2$, such that the moisture absorption per unit area of said sanitary napkin is not less than $7.2 \times 10^{-4}$ g/hr.cm$^2$, and the total amount of moisture absorption of said sanitary napkin is not less than 0.10 g/hr in an environment of 35° C./75% relative humidity.

2. The sanitary napkin as claimed in claim 1, wherein said liquid impermeable backsheet is a moisture permeable sheet having a moisture permeability of not less than 0.7 g/100 cm$^2$.hr.

3. The sanitary napkin as claimed in claim 1, wherein said absorbent member comprises said moisture absorbent material.

4. The sanitary napkin as claimed in claim 1, wherein said liquid permeable topsheet comprises said moisture absorbent material.

5. The sanitary napkin as claimed in claim 1, wherein said moisture absorbent material is formed into a moisture absorbent member that is joined to said absorbent member.

6. The sanitary napkin as claimed in claim 1, wherein said moisture absorbent material is formed into a moisture absorbent member that is interposed between said liquid permeable topsheet and said absorbent member.

7. The sanitary napkin as claimed in claim 1, wherein said moisture absorbent material is formed into a moisture absorbent member that is interposed between said absorbent member and said liquid impermeable backsheet.

* * * * *